United States Patent [19]

O'Brien

[11] Patent Number: 5,316,018
[45] Date of Patent: May 31, 1994

[54] DYNAMIC AMBULATORY METHOD AND APPARATUS FOR ASSESSMENT OF JOINTS OF THE HUMAN BODY

[76] Inventor: Todd D. O'Brien, 400 E. Remington Dr., Unit B-111, Sunnyvale, Calif. 94087

[21] Appl. No.: 47,266

[22] Filed: Apr. 12, 1993

[51] Int. Cl.[5] .......................................... A61B 5/103
[52] U.S. Cl. ................................................... 128/782
[58] Field of Search ..................... 128/774, 779, 782; 33/511, 512

[56] References Cited

U.S. PATENT DOCUMENTS

| | | | |
|---|---|---|---|
| 4,220,163 | 9/1980 | Malek Afzali | 128/774 |
| 4,436,099 | 3/1984 | Raftopoulos | 128/774 |
| 4,528,990 | 7/1985 | Knowles | 128/774 |
| 4,940,063 | 7/1990 | Challis | 128/774 |
| 5,027,688 | 7/1991 | Suzuki et al. | 128/782 |
| 5,156,161 | 10/1992 | Lollar | 128/774 |
| 5,188,121 | 2/1993 | Hanson | 128/782 |

FOREIGN PATENT DOCUMENTS

| | | | |
|---|---|---|---|
| 2249208 | 4/1974 | Fed. Rep. of Germany | 128/782 |
| 0997674 | 2/1983 | U.S.S.R. | 128/782 |
| 1233863 | 5/1986 | U.S.S.R. | 128/782 |

*Primary Examiner*—Max Hindenburg
*Attorney, Agent, or Firm*—John J. Leavitt; William A. Blake

[57] ABSTRACT

Presented is a dynamic apparatus for measuring and recording the range of angulation of an articular joint of the human body. The apparatus includes two separate assemblies for mounting on two relatively angularly articulable members on opposite sides of the joint between them. The two assemblies are interconnected across the joint in a manner to measure and record the extent of angulation of one member in relation to the other when the members are articulated.

7 Claims, 5 Drawing Sheets

U.S. Patent    May 31, 1994    Sheet 1 of 5    5,316,018
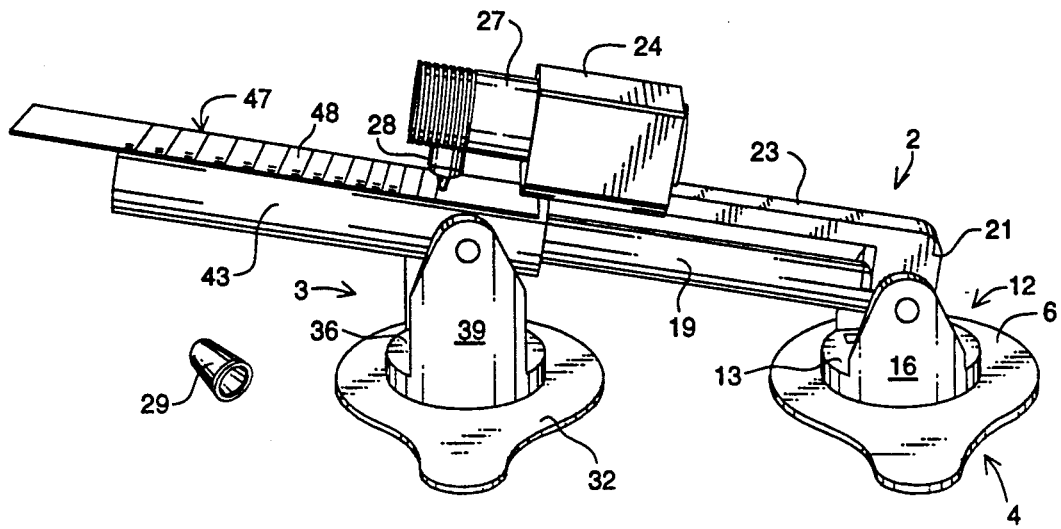
FIG_1
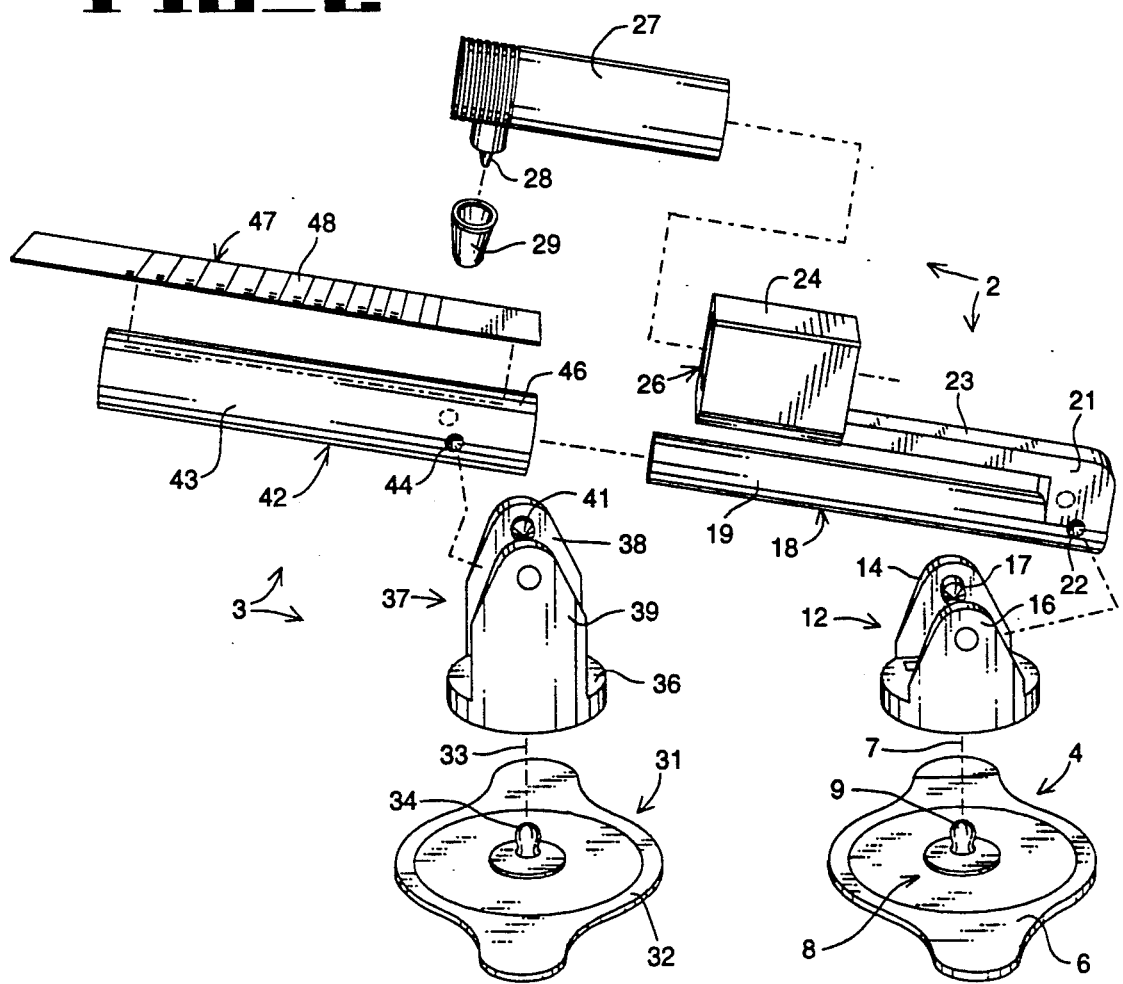
FIG_2

FIG_3
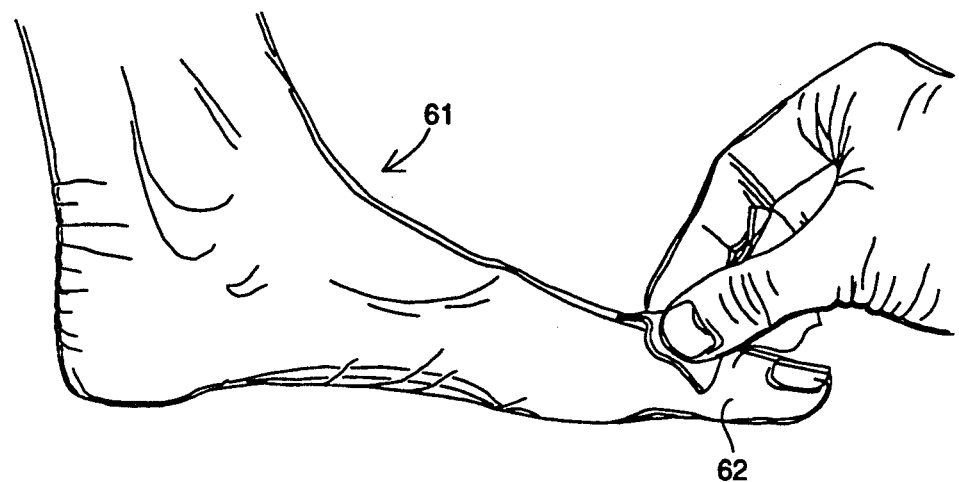
FIG_4
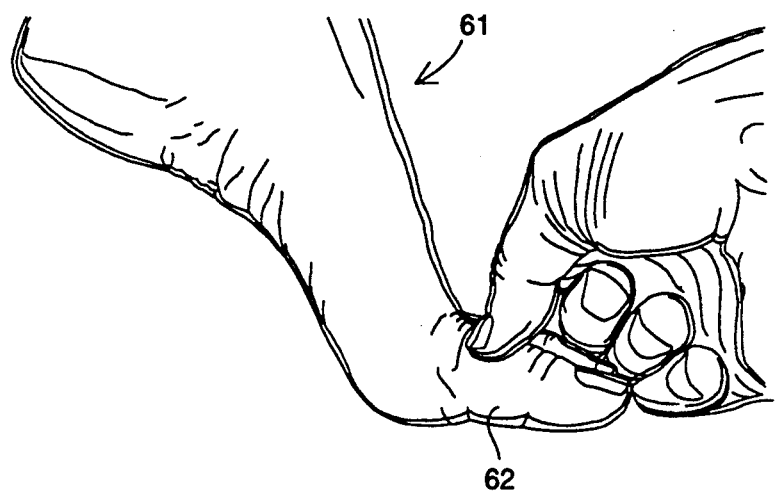
FIG_5
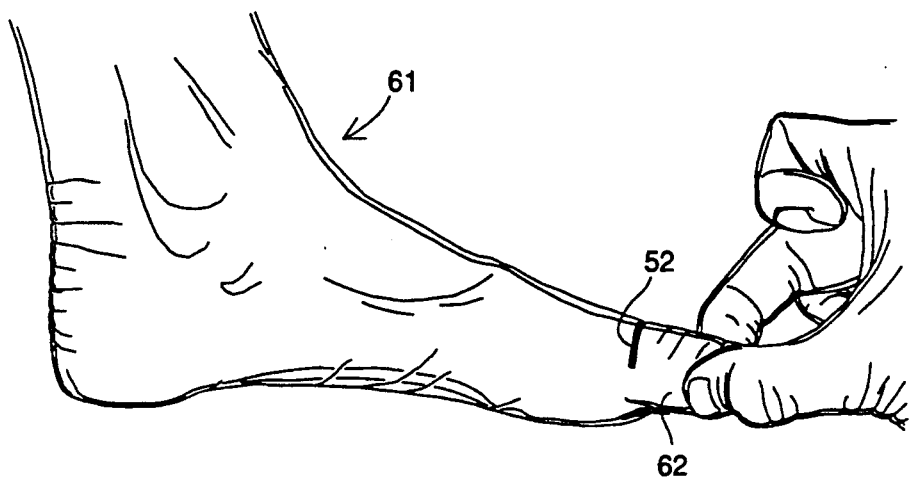

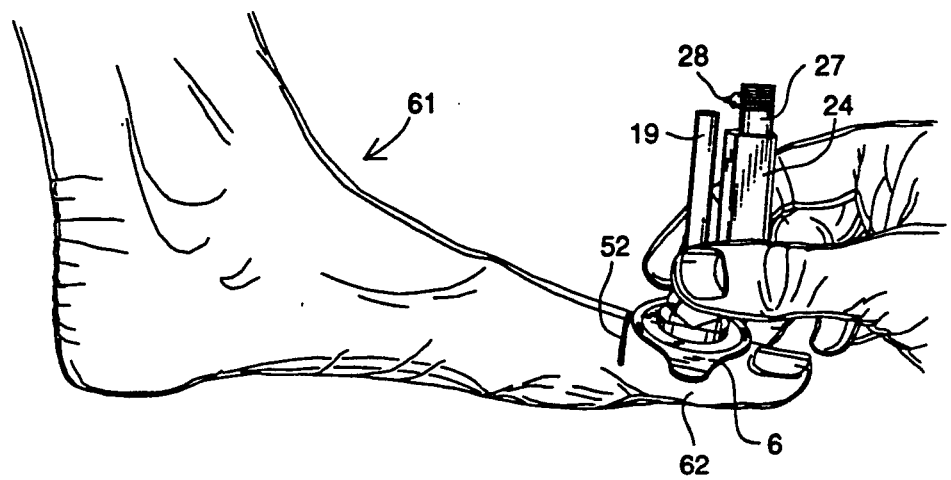
FIG_6
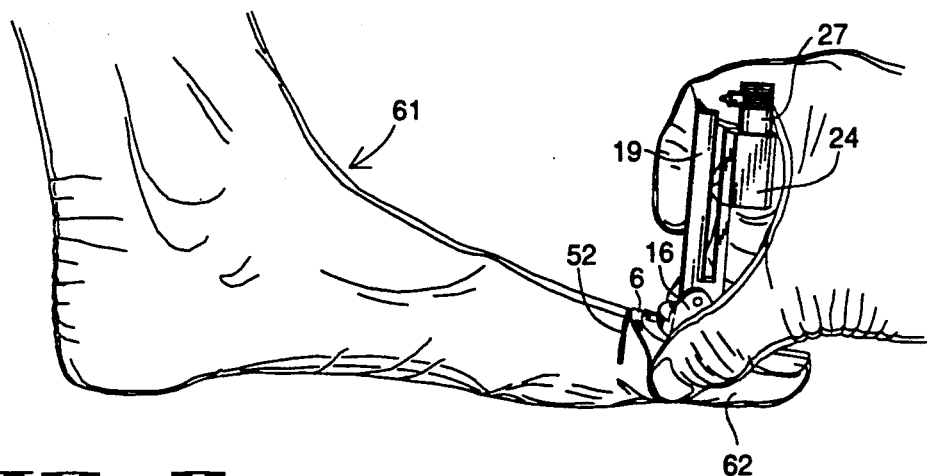
FIG_7
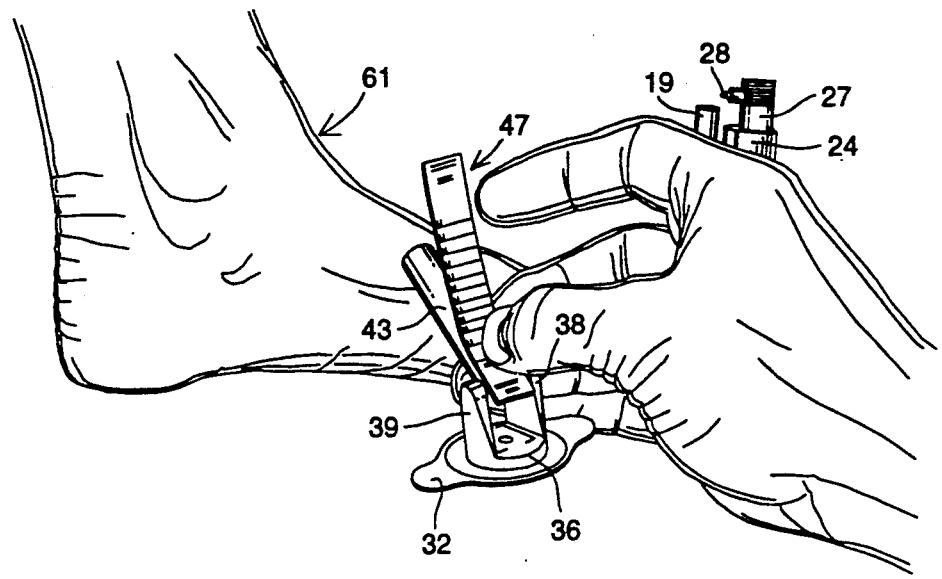
FIG_8

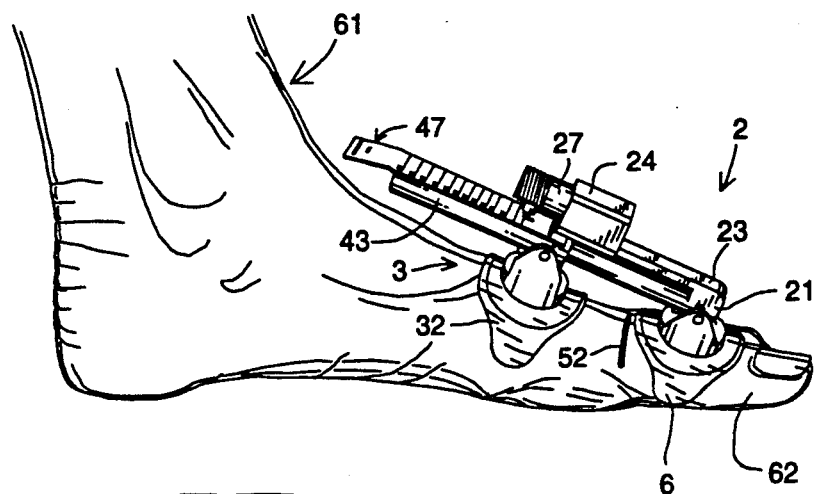
FIG_9
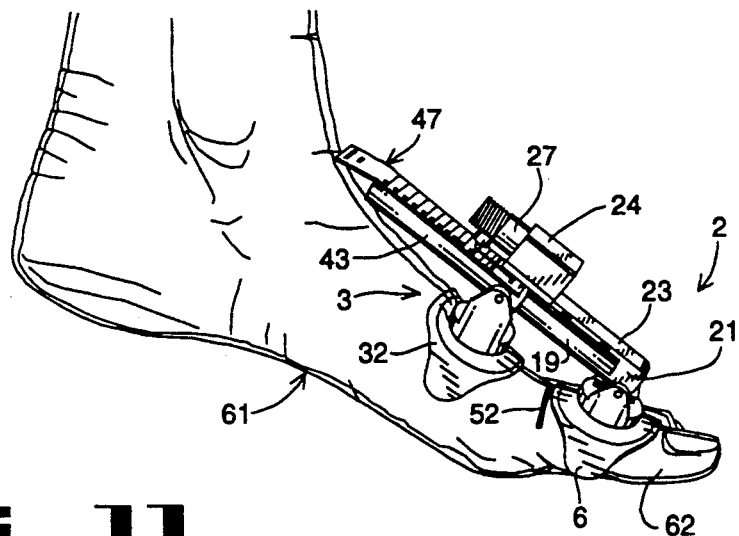
FIG_10
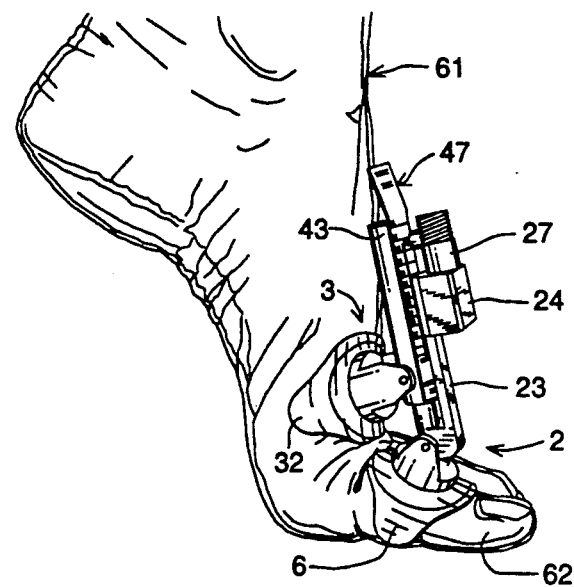
FIG_11

FIG_12
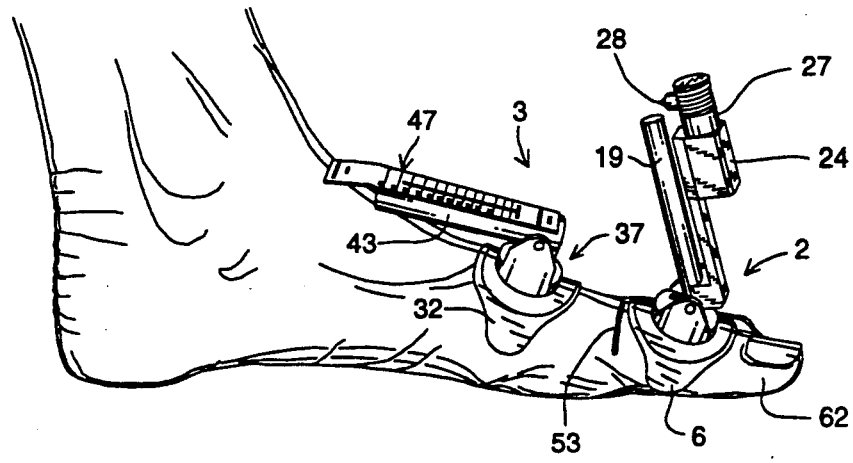
FIG_13
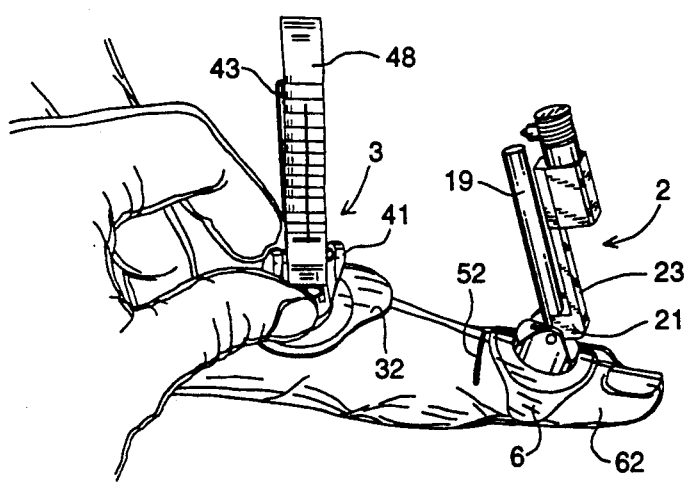
FIG_14
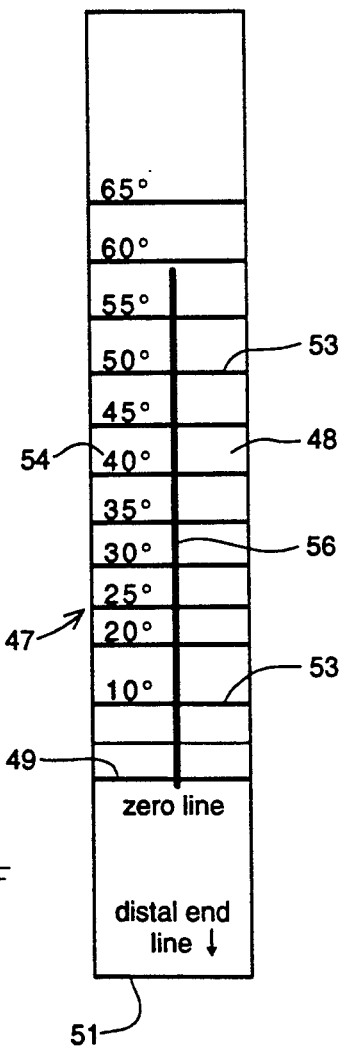

DYNAMIC AMBULATORY METHOD AND APPARATUS FOR ASSESSMENT OF JOINTS OF THE HUMAN BODY

BACKGROUND OF THE INVENTION

1. Field of the Invention

This invention relates to devices and apparatus for assessement of the pivotal movement of joints of the human body, and particularly to a method and apparatus for toe-off assessement of the first metatarsophalangeal joint of the human foot.

2. Description of the Prior Art

Because of the wear and tear of the many joints of the human body, these joints are frequently injured and require medical attention of one form or another. The prior art is replete with devices and apparatus for assessing and assisting in the treatment of injured joints of the human body. A preliminary patentability and novelty search conducted through Classes 33, 73 and 128, including many sub-classes in these primary classes, has revealed the existence of the following U.S. Pat. Nos.:

| | | |
|---|---|---|
| 1,590,499 | 3,358,373 | 4,416,292 |
| 4,436,099 | 4,771,548 | 4,802,494 |
| 4,804,001 | 4,905,560 | 4,986,280 |

The patents listed above were found in a search for patent literature that relates particularly to the first metatarsophalangeal joint. Many other patents are known to exist that pertain to other joints of the human body. For instance, the following additional patents that relate to various joints of the human body and their assessement and treatment are known to exist.

| | | |
|---|---|---|
| 4,745,930 | 3,553,590 | 4,444,205 |
| 4,461,085 | 4,883,069 | 4,940,063 |
| 4,201,226 | 4,436,099 | 4,800,897 |
| 4,897,927 | | 4,897,931 |

In addition to the patent literature noted above, technical articles are also known to exist that relate to this subject. Two such technical articles include *Goniometric Reliability in a Clinical Setting, Elbow and Knee Measurements*, authored by Jules M. Rothstein et al, and published in Physical Therapy, Volume 63/Number 10, October 1983. Another technical article appeared in Clinics in Podiatric Medicine and Surgery, Volumne 3, No. 4, October 1986, and entitled *Tools for Biomechanical Analysis of the Foot*, written by James G. Richards, Ph.D.

One of the reasons that there is a plethora of prior art and technical articles that relate to the subject of joint movement, joint assessment and joint treatment, is that the nature of the human body requires different ranges of motion in the different joints of the human body, and these ranges vary from individual to individual. When those ranges of movement are restricted for some reason, or extended beyond their normal range, injury to the joint can and may occur, necessitating assessment of the joint to determine the existence of damage or injury, the extent thereof and the treatment options presented by the injury, if any, or an abnormality that may exist.

Of all of the joints of the human body, the first metatarsophalangeal joint is among the most frequently treated locations in the foot. Such afflictions as hallux abducto valgus, hallux limitus and rigidus osteoarthritis and rheumatoid arthritis often affect the first metatarsophalangeal joint. In assessing the function of this joint it is important to determine its range of motion. This is conventionally accomplished by examining the patient in the non-weight bearing setting using a goniometer to measure the angulation between the first metatarsal and proximal phalanx. This method limits evaluation of the dorsiflexion and plantarflexion range of motion to a non-weight bearing situation. However, this method is unable to determine the first metatarsophalangeal joint functional range of motion during gait, as when walking, with the entire body weight imposed on the joint.

Current methods of obtaining information of this nature include electrogoniometry and high-speed cinematography. These "high-tech" methods of assessing first metatarsophalangeal joint functional range of motion require a significant financial investment on the part of the clinician or researcher seeking to utilize them because the equipment necessary to utilize these methods is very expensive. Accordingly, it is one of the important objects of the present invention to provide a system and method enabling the measurement of the first metatarsophalangeal joint functional range of motion in a more cost effective manner.

Another clinical gait parameter determined by electrogoniometry and high-speed cinematography is the quantification of the propulsive phase of gait. The propulsive phase of gait is defined as the time interval from heel lift to toe-off. It is therefore another object of the present invention to provide a method of recording the time interval in which the first metatarsal is rotating over the proximal phalanx so as to correlate this time interval to the propulsive phase of gait.

Yet another object of the invention is to provide a means and method for measurement of the first metatarsophalangeal joint range of motion during gait, and quantification of the propulsive phase of gait. Fulfillment of this object is accomplished by the generation of a curve that represents the angular velocity of the first metatarsal during the propulsive phase of gait. While a method has been devised to generate such curves, the clinical value of these curves is unknown at this time. It is hypothesized that these curves may provide a method for cataloging patterns that correlate with specific pathological entities. Clinical research must be conducted to investigate this possibility.

During natural gait, lift off of the heel from the supporting surface of the foot results in the development of angulation between the first metatarsal and proximal phalanx. Through conventional methods, the pivot point of the metatarsal with respect to the proximal phalanx may be located quite accurately. From such location of the pivot point, a measurement may be taken parallel to the first metatarsal and a second measurement may be taken parallel to the proximal phalanx. The distances on the foot represented by these measurements are generally variable for each individual, but for a specific individual, these measurements or distances measured on the respective portions of the foot on either side of the joint line, may be considered to be fixed distances which are correlated to two sides of a triangle converging at the joint line, the third side of the triangle being a variable measurement or distance that joins the distal ends of the two measurements on either side of the joint line or pivot point of the first metatarsophalangeal joint. It will of course be obvious that geometrically, the third side of the triangle, or length measurement of this third side of the triangle thus formed, will vary according to the degree of angulation of the first metatarsal to the proximal phalanx. Accordingly, one of the important objects of the present invention is the provision of a dynamic ambulatory method and apparatus for toe-off assessment of the first metatarsophalangeal joint during normal gait.

Still another object of the invention is the provision of a dynamic ambulatory method and apparatus for toe-off assessement of the first metatarsophalangeal joint that utilizes the Law of Cosines to calculate the angulation between the first metatarsal and proximal phalanx at toe-off.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, the dynamic ambulatory method and apparatus for toe-off assessment of the first metatarsophalangeal joint involves accurately locating the joint line of the distal side of the first metatarsophalangeal joint, i.e., the proximal articular surface of the proximal phalanx. This joint line is marked as a reference on the patients foot. Accurate location of this line is necessary for proper functioning of the apparatus forming the subject matter of this invention. To accurately locate the joint line, it is recommended that the first metatarsophalangeal joint be pivoted while the patient is standing. This is accomplished by requesting the patient to plantarflex at the ankle joint and then return to neutral position while the clinician palpates and locates the distal side of the joint line. Having accurately located and marked the location of the distal side of the joint line, with the patient standing, the distal assembly portion of the apparatus, including a base unit, is affixed to the dorsal aspect of the hallux. The base unit serves as a mechanical anchor on the dorsal aspect of the hallux, and must touch or be coincident with the distal side of the joint line that has been marked on the patient's foot. The proximal assembly portion of the apparatus that cooperates with the distal assembly portion to determine the degree of angulataion is next provided with a removable label on which is printed a graduated scale commencing at a "zero" line and having progressive degree increments marked thereon that progress from the "zero" line. The distal assembly portion of the apparatus includes an ink pen the tip of which is lined up with the "zero" line on the label. While maintaining this alignment of the tip of the pen with the "zero" line of the proximal assembly portion of the apparatus, the proximal assembly portion of the apparatus is affixed to the first metatarsal region utilizing a base similar to the base of the distal assembly portion. When the apparatus, both distal and proximal assembly portions are assembled and firmly attached to the patient's foot, the patient is requested to walk ten to fifteen (10–15) steps at a normal cadence. Thereafter, the distal and proximal assembly portions of the apparatus are disengaged and removed from the patient's foot. The label is read and removed from the apparatus and the label is placed in the patient's chart to serve as a permanent record of the assessment. The apparatus may now be cleaned and provided with a new label in preparation of use of the apparatus with another patient. Structurally, with respect to the distal assembly portion of the apparatus that is fixed to the dorsal aspect of the hallux, the base is adhesively secured to the hallux in proper position, and includes a fastener element adapted to detachably engage a trunnion that provides a pivot axis for an elongated member on which is mounted a marking device such as an ink pen. With respect to the proximal assembly portion of the apparatus that is attached to the dorsal aspect of the first metatarsal on the opposite side of the joint line from the distal assembly portion of the apparatus, this assembly also includes a base similar to the base that serves to mount the distal assembly portion that is mounted on the hallux, and also includes a fastener element that detachably engages a trunnion member on which is pivotally mounted an elongated tubular member. The label is mounted on the elongated tubular member and the elongated member of the distal assembly portion of the apparatus is telescopically inserted into the interior of the tubular member of the proximal assembly portion. Thus, when dorsiflexion of the first metatarsophalangeal joint occurs, the elongated member of the distal assembly portion of the apparatus telescopically slides in relation to the elongated tubular member of the proximal assembly portion of the apparatus, and the marking pen accurately marks on the label scale the degree of angulation of the first metatarsophalangeal joint.

BRIEF DESCRIPTION OF THE DRAWINGS

FIG. 1 is a perspective view of the dynamic ambulatory apparatus for toe-off assessment of the invention, shown apart from a patient's foot.

FIG. 2 is a perspective view in exploded form of the various components that make up the apparatus of the invention.

FIG. 3 is a perspective view illustrating the manner in which the region on the patient's foot associated with the hallux and the first metatarsophalangeal joint is cleansed, preferably with alchohol, prior to location of the joint line of the distal side of the first metatarsophalangeal joint.

FIG. 4 is a view illustrating the method by which the joint line of the first metatarsophalangeal joint is located.

FIG. 5 is a perspective view that illustrates the reference line that is drawn on the patient's toe to mark the exact location of the joint line of the first metatarsophalangeal joint.

FIG. 6 is a perspective view illustrating the manner in which the distal assembly portion of the apparatus is affixed to the dorsal aspect of the hallux.

FIG. 7 is a perspective view illustrating completion of the application of the distal assembly portion of the apparatus to the dorsal aspect of the hallux in relation to the line on the patient's foot that marks the accurate location of the joint line of the first metatarsophalangeal joint.

FIG. 8 is a perspective view that illustrates placement of the graduated label on the elongated tubular member of the proximal assembly portion of the apparatus prior to application of the proximal assembly to the patient's foot.

FIG. 9 is a perspective view that illustrates the toe-off assessment apparatus installed on a patient's foot while the foot is in a relaxed or neutral postion.

FIG. 10 is a perspective view that illustrates the commencement of dorsiflexion of the first metatarsophalangeal joint, indicating the relative movement between the marker mounted on the distal assembly portion of the apparatus and the label mounted on the elongated tubular member of the proximal assembly portion of the apparatus.

FIG. 11 is a perspective view that illustrates maximum dorsiflexion of the first metatarsophalangeal joint of the patient, accompanied by repositioning of the marker in relation to the label to record the degree of such dorsiflexion.

FIG. 12 is a perspective view that illustrates the patient's foot returned to a neutral postion, with the distal assembly portion of the apparatus now detached from the proximal assembly portion of the apparatus in preparation of the removal of the apparatus from the patient's foot.

FIG. 13 is a fragmentary perspective view that illustrates the manner in which the proximal assembly portion of the apparatus may be rotated on the base to enable observation of the length of the line that has been marked on the scale by the marker mounted on the distal assembly portion of the apparatus.

FIG. 14 is a plan view of one of the labels, shown in enlarged scale, and indicating the manner in which the line marked on the scale extends from the "zero" line on the scale to a graduation that indicates the extent of dorsiflexion of the first metatarsophalangeal joint.

DESCRIPTION OF THE PREFERRED EMBODIMENT

In terms of greater detail, while the subject matter of this invention has been described and illustrated with respect to the first metatarsophalangeal joint of the human foot, it should be understood at the outset that the method and apparatus is contemplated for use in the assessment of joint function at the ankle, knee, elbow and finger joints, in addition to the first metatarsophalangeal joint. It is recognized that slight modifications might have to be made to the structural aspects of the apparatus to accommodate these different joints, and that procedural steps might have to be modified with respect to the method, but it is believed and intended that the method and apparatus for these additional joints of the human body are included within the scope of the appended claims.

Referring to FIGS. 1 and 2, it will be seen that the dynamic ambulatory apparatus for toe-off assessment of the first metatarsophalangeal joint comprises a distal assembly portion designated generally by the numeral 2, adapted to cooperate and function with a proximal assembly portion designated generally by the numeral 3. Referring first to the distal assembly portion 2, it will be seen that this assembly includes a base member designated generally by the numeral 4 and comprising a flexible member 6 having a generally circular configuration symmetrical about a central axis (FIG. 2), preferably formed from a non-resilient yet flexible synthetic resinous material, and provided on its undersurface with a suitable adhesive that, prior to application of the apparatus, is protected by an appropriate protective sheet of material that may be peeled from the adhesive coated base material 6 so as to expose the adhesive coated undersurface of the base material for application to the patient's foot. Mounted coincident with the central axis of the base 4 is a fastener element designated generally by the numeral 8, and in this embodiment of the invention constituting a resilient snap-fastener element or so called "glove" fastener 9, adapted to detachably engage with a complementary fastener element (not shown) formed on the central axis of the trunnnion structure designated generally by the numeral 12. The trunnion structure includes a base portion 13 that serves as a mounting base for the fastener element that engages the fastener element 9, and in most instances the fastener element in the base 13 may constitute an appropriate aperture that frictionally engages the fastener element 9 when the latter is inserted into the aperture. Projecting from opposite peripheral portions of the base 13 of the trunnion structure are laterally spaced lugs 14 and 16 each of which is provided with a mutually reaching stub shaft 17 the axes of which are in alignment, and perpendicular to the vertical axis of the trunnion structure and the axis 7.

The distal assembly portion of the structure also includes an elongated member designated generally by the numeral 18, and including an elongated cylindrical rod 19 extending cantilever fashion from a base portion 21 having formed in opposite sides thereof aligned recesses 22 for reception of the aligned stub shafts 17 so as to mount the base member 21 and the appended cylindrical rod 19 pivotally on the trunnion structure 12. Extending integrally from the base member 21 is a second cantilever beam 23 on the free end of which is mounted a housing member 24 adapted to receive therewithin in a longitudinally extending recess 26, the cylindrical body 27 constituting a pen holder for pen 28. An appropriate cap 29 is provided for the pen 28. The pen holder 27 slips into the recess 26 with sufficient frictional contact that it will remain in the position in which it is adjusted. Preferably, the individual components of the distal assembly portion of the apparatus are fabricated from an appropriate synthetic resinous material. Where necessary, the base 4 may be fabricated from materials that are disposable and replaceable by a substitute base so as to maintain a sterile relationship between the base 4 and the patient's foot.

Again referring to FIGS. 1 and 2, but now focusing on the proximal assembly portion designated generally by the numeral 3, it will be seen that the proximal assembly portion also includes a base, designated generally by the numeral 31, similar in its construction to the base 4, and including a flexible yet non-resilient member 32 formed generally symmetrical about a central axis 33 and having mounted axially thereon a snap-fastener element 34 adapted to detachably engage a complementary fastener element (not shown) formed or mounted on the base 36 of a second trunnion structure designated generally by the numeral 37. The trunnion structure 37 includes the base 36 and a pair of laterally spaced lugs 38 and 39 extending integrally from opposite peripheral portions of the base 36 and each provided with a stub shaft 41 the axes of which are aligned, and each of which projects a short distance beyond the inner surface of the lugs 38 and 39.

The proximal assembly portion of the apparatus also includes a tubular sheath designated generally by the numeral 42 and constituting an elongated generally cylindrical shell or sheath 43 suitably fabricated from a synthetic resinous material and having an inner periphery proportioned to freely slidably accept the elongated member 19 of the distal assembly portion of the apparatus. The tubular sheath 42 is pivotally mounted on the trunnion structure 37 by engagement of the stub shafts 41 with appropriate recesses 44 formed diametrically in the side walls of the sheath 42 and dimensioned to receive the stub shafts 41. Preferably, there is a flat surface 46 formed on the tubular sleeve 43, the plane of the flat surface 46 being generally parallel to the axes of the recesses 44 formed in the sleeve. Adapted to be releasably mounted on the flat surface 46 of the tubular sleeve 43 is a label designated generally by the numeral 47 and including an elongated flat strip 48 formed from appropriate card stock that will receive a marking ink. As illustrated in FIG. 14, the label 47 is pre-printed with appropriate indicia including a zero line 49, and an end edge 51 adapted to be aligned with the associated end of the tubular sleeve 43. The label 47 also bears graduations 53 spaced along the strip 48 at intervals that are correlated to the Law of Cosines, each of the graduations 53 further being designated by an appropriate indicia 54 designating the degree of angulation between the longitudinal axes of the first metatarsal and the proximal phalanx. On the label illustrated in FIG. 14, the line 56 represents the line that is imposed on the strip label by the pen marker 28 upon maximum dorsiflexion as illustrated in FIG. 11.

Referring to FIGS. 3 through 5, it will there be seen from FIG. 3, that the patient's foot, designated generally by the numeral 61, particularly in the dorsal aspect of the first metatarsophalangeal joint, is appropriately cleansed with a soft sponge or other material suitably saturated with an appropriate antiseptic such as alcohol. Alcohol is preferred because it does not leave a residue on the dorsal aspect of the hallux or the first metatarsal region. Following cleansing, the patient is requested to plantarflex the ankle joint so as to cause dorsiflexion of the first metatarsophalangeal joint as illustrated in FIG. 4. During this maneuver, the clinician palpates the region of the first metatarsophangeal joint, and determines the exact location of the joint line between the first metatarsal and the proximal phalanx. Upon accurately determining the joint location, the clinician then marks the location of the joint with the joint line mark 52 so that the toe-off assessment apparatus of the invention may be applied to the dorsal aspect of the hallux and to the first metatarsal region while giving effect to the location of the joint line 52.

Thus, referring to FIG. 6, it will be seen that with the patient's foot 61 in a neutral position on a supporting surface, and after having removed the protective covering from the adhesive backing on the base 6, the distal assembly portion 2 is applied to the dorsal aspect of the hallux 62 so that the associated edge of the base 6 coincides with the joint line 52 as shown. This placement is important because the longitudinal distance between the vertical axis 7 of the fastener 9 and the location of the joint line 52 is one of the dimensions that determines the angulation of the first metatarsophalangeal joint that is ultimately marked on the label 47. It will be noted from FIG. 6 that during this application, the distal assembly portion of the apparatus is arranged so that the elongated slide rod 19 extends generally vertically upwardly or generally perpendicular to the longitudinal axis of the hallux. When properly placed, as illustrated in FIG. 6, the laterally extending portions of the base 6, are pressed firmly around the base of the hallux as illustrated in FIG. 7. The adhesive on the underside of the base 6 thus firmly and yet detachably secures the distal assembly portion to the dorsal aspect of the hallux as shown.

Referring now to FIG. 8 of the drawings, it will be seen that the proximal assembly portion designated generally by the numeral 3 has been partially assembled by engagement of the stub shafts 41 in the recesses 44 of the tubular member 43, and the label 47 is being applied to the exterior surface 46 of the tubular member. In applying the label 47 to the tubular member 43, it should be remembered that the distal end edge 51 of the label should be lined up with the end of the tubular member 43 nearest the pivotal axis provided by the stub shafts 41 and recesses 44. This relationship is illustrated in exploded form in FIG. 2.

Following application of the label 47 to the proximal assembly portion of the apparatus, the elongated slide member 19 of the distal assembly portion 2 is inserted into the interior of the elongated tubular member 43. There follows removal of the protective cap 29 from the marker member 28. The point of the marker member 28 is aligned with the "zero" line 49 on the label, and the two portions 2 and 3 are retained in this position while the protective coating is removed from the underside of the base member 32 to expose the adhesive layer thereon. Next, the base 32 is applied to the dorsal aspect of the first metatarsal as illustrated in FIG. 9, the while making sure that the patient's foot 61 is in a neutral position as illustrated, and that the marker point 28 rests on the zero line 49 of the label. The base 32 of the proximal assembly portion 3 is pressed tightly around the patient's foot to fix the base to the skin which has previously been cleansed. This relationship of the apparatus is illustrated in FIG. 9.

Having attached the apparatus to the patient's foot as illustrated in FIG. 9, the patient is now requested to plantarflex the ankle joint, which results in dorsiflexion of the first metatarsophalangeal joint as illustrated in FIG. 10. Such dorsiflexion causes the angle between the first metatarsal and the proximal phalanx, the apex of which angle coincides with the joint line 52, to change from "zero" degrees (which essentially is 180 degrees) to a variable angulation as the heel and the first metatarsal pivot about the joint line 52. As pivotal action continues, the marker point 28 glides over the graduations of the label 47, marking the degree of angulation of dorsiflexion as dorsiflexion progresses. Ultimately, as illustrated in FIG. 11, the patient will have caused maximum dorsiflexion of the first metatarsophalangeal joint, and the marker point 28 will have progressed to its maximum extent along the graduated strip 48.

Following this exercise, if it appears to be advisable, the clinician may request the patient to walk at normal cadence ten or fifteen steps so as to determine the path and extent of the line 56 on the graduated scale 47 during normal gait by the patient. Subsequently, with the patient's foot returned to neutral position as illustrated in FIG. 10, the pen holder 27 is rotated to expose the marker point 28 and the protective cap 29 is applied to the marker point. The basis 6 and 32 of the apparatus may now be detached from the patient's foot, and the distal assembly portion dissassembled from the proximal assembly portion by extraction of the guide rod 19 from the interior of the elongated hollow member 43. Additionally, the label 47, now marked with the extent of dorsiflexion of the first metatarsophalangeal joint, is removed from the tubular member 43, and evaluated by the clinician. The results of such evaluation are normally entered in the patient's chart, and the label itself is included in the chart for future reference and comparison with other similar labels that might be generated in subsequent assessment sessions.

Having thus described the invention, what is believed to be new and novel and sought to be protected by letters patent of the United States is as follows.

I claim:

1. A dynamic ambulatory apparatus for measuring and recording during gait the range of angulation of the first metatarsophalangeal joint of the human body disposed between the relatively angularly articulable first metatarsal and the proximal phalanx of the human foot, comprising:
   a) a distal assembly portion of the apparatus adapted for detachable engagement to said angularly articulable proximal phalanx at a location spaced from said first metatarsophalangeal joint;
   b) a proximal assembly portion of the apparatus cooperatively related to said distal assembly portion of the apparatus and adapted for detachable engagemnt to said angularly articulable first metatarsal at a location spaced on the opposite side of said first metatarsophalangeal joint from said proximal phalanx; and
   c) means disposed between said distal assembly portion and said proximal assembly portion operable when said first metatarsal and said proximal phalanx are angularly articulated during gait to measure and record the extent of angulation therebetween.

2. The dynamic ambulatory apparatus as defined in claim 1, wherein said means for measuring and recording the angulation during gait of said relatively articulable first metatarsal and proximal phalanx in relation to one another comprises a scale on said proximal assembly portion having indicia thereon defining a range of said angulation measurement, and means on said distal assembly portion movable in relation to said scale to an extent correlated to said angulation whereby the extent of said angulation is measured and recorded.

3. A dynamic apparatus for measuring and recording the range of angulation of an articular joint of the human body disposed between two relatively angularly articulable members, comprising:
   a) a distal assembly portion of the apparatus adapted for detachable engagement to one of said angularly articulable members at a location spaced from said first joint;
   b) a proximal assembly portion of the apparatus cooperatively related to said distal assembly portion and adapted for detachable engagement to the other of said angularly articulable members at a location spaced on the opposite side of said joint; and
   c) means disposed between said distal assembly portion and said proximal assembly portion operable when said members are angularly articulated to measure and record the extent of angulation therebetween;
   d) said distal assembly portion of the apparatus including a base member adapted for detachable attachment to the surface of one of said articulable members on the distal side of said joint, a trunnion structure detachably mounted on said base member, a slide rod pivotally mounted on said trunnion structure, a cantilever beam pivotally mounted on said trunnion structure in spaced parallelism with said slide rod and having a free end spaced from said trunnion structure, and marker means mounted on the free end of said cantilever beam and operatively associated with said proximal assembly portion whereby angular articulation of said articulable members effects generation by said marker of indicia indicative of the extent of said angular articulation.

4. The dynamic apparatus as defined in claim 3, wherein a graduated scale is detachably mounted on said proximal assembly portion, and said marker means marks a line on said scale indicative of the extent of said angular articulation.

5. A dynamic apparatus for measuring and recording the range of angulation of an articular joint of the human body disposed between two relatively angularly articulable members, comprising:
   a) a distal assembly portion of the apparatus adapted for detachable engagement to one of said angularly articulable members at a location spaced from said joint;
   b) a proximal assembly portion of the apparatus cooperatively related to said distal assembly portion and adapted for detachable engagement to the other of said angularly articulable members at a location spaced on the opposite side of said joint; and
   c) means disposed between said distal assembly portion and said proximal assembly portion operable when said members are angularly articulated to measure and record the extent of angulation therebetween;
   d) said proximal assembly portion of the apparatus includes a base member adapted for detachable attachment to the surface of one of said articulable members on the proximal side of said joint, a trunnion structure detachably mounted on said base trunnion structure, and a graduated scale detachably mounted on said elongated tubular sheath and including indicia representing a measurement of the extent of angular articulation between said articulable members.

6. A dynamic apparatus for measuring and recording the range of angulation of an articular joint of the human body disposed between two relatively angularly articulable members, comprising:
   a) a distal assembly portion of the apparatus adapted for detachable engagement to one of said angularly articulable members at a location spaced from said joint;
   b) a proximal assembly portion of the apparatus cooperatively related to said distal assembly portion and adapted for detachable engagement to the other of said angularly articulable members at a location spaced on the opposite side of said joint; and
   c) means disposed between said distal assembly portion and said proximal assembly portion operable when said members are angularly articulated to measure and record the extent of angulation therebetween;
   d) said distal assembly portion of the apparatus including a base member adapted for detachable attachment to the surface of one of said articulable members on the distal side of said joint, a trunnion structure detachably mounted on said base member, a slide rod pivotally mounted on said trunnion structure in spaced parallelism with said slide rod and having a free end spaced from said trunnion structure, and marker means mounted on the free end of said cantilever beam and operatively associated with said proximal assembly portion whereby angular articulation of said articulable members effects generation by said marker of indicia indicative of the extent of said angular articulation;
   e) said proximal assembly portion of the apparatus including a base member adapted for detachable attachment to the surface of one of said articulable members on the proximal side of said joint, a trunnion structure detachably mounted on said base member, an elongated tubular sheat pivotally mounted on said trunnion structure, and a graduated scale detachably mounted on said elongated tubular sheath and including indicia representing a measurement of the extent of angular articulation between said articulable members.

7. The dynamic apparatus as defined in claims 6, 8, 9, or 10, wherein said articulable members comprise the hallux to which said distal assembly portion is detachably attached and the first metatarsal region of the foot on the proximal side of the first metatarsophalangeal joint and to which the proximal assembly portion is detachably attached.

* * * * *